(12) United States Patent
Yardan et al.

(10) Patent No.: US 7,543,587 B2
(45) Date of Patent: Jun. 9, 2009

(54) MEDICAL DRAPE

(75) Inventors: Stephen J. Yardan, Branford, CT (US); Walter McGregor, Flemington, NJ (US); David C. Novicki, Orange, CT (US)

(73) Assignee: Block Island Technologies, LLC, Branford, CT (US)

( * ) Notice: Subject to any disclaimer, the term of this patent is extended or adjusted under 35 U.S.C. 154(b) by 147 days.

(21) Appl. No.: 11/652,343

(22) Filed: Jan. 11, 2007

(65) Prior Publication Data

US 2008/0168995 A1    Jul. 17, 2008

(51) Int. Cl.
*A61B 19/00* (2006.01)
*A61B 19/08* (2006.01)
*B65D 33/16* (2006.01)

(52) U.S. Cl. .................. 128/849; 128/856; 383/66; 383/907

(58) Field of Classification Search .................. 128/849, 128/853, 856, 882; 383/906, 907, 66; 602/3; 2/167; 604/356, 293, 408; 119/725, 726, 119/814, 816, 856
See application file for complete search history.

(56) References Cited

U.S. PATENT DOCUMENTS

| 4,308,864 | A | | 1/1982 | Small et al. |
| 4,966,135 | A | | 10/1990 | Renfrew |
| 5,178,162 | A | * | 1/1993 | Bose .......................... 128/849 |
| 5,312,385 | A | * | 5/1994 | Greco .......................... 604/356 |
| 2006/0291755 | A1 | * | 12/2006 | Olin et al. ..................... 383/66 |

* cited by examiner

*Primary Examiner*—Patricia M Bianco
*Assistant Examiner*—Victoria Hicks
(74) *Attorney, Agent, or Firm*—Robert H. Bachman

(57) ABSTRACT

A medical drape, particularly a surgical drape, having a front side and rear side, with the front side being connected to the rear side to form an enclosure to enclose a patient's extremity. The front side includes an open end which is closable around the patient's extremity, and the rear side is closed by a closed base wall. The base wall includes a first upper portion and a second lower portion, and includes a tapered base wall between the first upper portion and the second lower portion for fluid flow towards the second lower portion. A drain is provided adjacent the second lower portion for drainage of fluids that collect inside the drape.

12 Claims, 3 Drawing Sheets

MEDICAL DRAPE

BACKGROUND OF THE INVENTION

The present invention relates to medical drapes for enclosing a patient's extremity, especially during a surgical procedure. More specifically, the present invention relates preferably to surgical drapes which enclose that portion of a patient's limb which is undergoing a surgical procedure to collect and drain fluids during a surgical procedure.

During a surgical procedure on an arm or leg, fluids often must be collected that are developed during the procedure. For example, sterile irrigation fluids are often used to clean a wound or remove foreign matter from the wound. During irrigation a significant amount of the material will splash onto the physician and/or the assistants. The patient's blood, which may be contaminated, also must be collected and prevented from contaminating the physician and/or the assistants.

In addition, during wound treatment, in general it is desirable to collect fluids that may develop during wound treatment and/or during patient recovery and prevent contamination thereby.

It is desirable to provide an effective means to collect and drain fluids which are developed during a surgical procedure on a patent's extremity, and during wound treatment in general, without contaminating personnel, including the physician and/or the physician's assistants during a surgical procedure, and to do so in an effective and convenient way.

Accordingly, it is a principal object of the present invention to provide a medical drape that encloses a patient's extremity during a surgical procedure, or during wound treatment and patient recovery in general.

It is a further object of the present invention to provide a surgical drape as aforesaid which collects and dispenses fluids for disposal that are developed in a surgical procedure, or wound treatment in general, in a safe, effective and convenient way.

It is a still further object of the present invention to provide a medical or surgical drape as aforesaid wherein the wound fluids and surgical fluids are readily collected and may be fully and completely disposed of, all in a safe and effective way.

Further objects and advantages of the present invention will appear hereinbelow.

SUMMARY OF THE INVENTION

In accordance with the present invention the foregoing objectives are readily obtained.

The medical drape of the present invention comprises:

an elongated tube having a front side and a rear side, said front and rear sides being connected together to form an enclosure to enclose a patient's extremity, as during wound treatment or surgery on said extremity;

wherein said front side includes an open end with means to close said open end around said patient's extremity, and said rear side being closed by a closed base wall;

said base wall having a first upper portion and a second lower portion, said upper and lower portions being spaced from each other, and including a tapered base wall between the first upper portion and second lower portion for fluid flow towards the second lower portion; and a drainage means adjacent said second lower portion for drainage of fluids that collect inside said drape.

Preferably, the tapered base wall extends generally at an angle with respect to the first upper portion to facilitate drainage, and preferably the tapered base wall extends generally inwardly towards the front side. The tapered base wall preferably extends continuously at said angle from said first upper portion to said second lower portion.

The open end is desirably closable around the extremity, as the arm or leg. For example, the open end can be closed by a pull or an adhesive closure.

The first upper portion desirably has a triangular configuration. In addition, the elongated tube has a side wall connecting the front side with the rear side, and the rear side base wall extends generally at an angle with respect to the side wall.

The elongated tube is a liquid resistant material, preferably a plastic material, as a transparent or translucent plastic, as polyethylene or polyurethane, although other materials can be used as vinyl or rubber materials.

The present invention is highly advantageous, particularly in a surgical setting. It permits the easy and safe collection and disposal of fluids from a wound or in a surgical operation in a safe, clean and expeditious manner.

Further objects and advantages of the present invention will appear hereinbelow.

BRIEF DESCRIPTION OF THE DRAWINGS

The present invention will be more readily understandable from a consideration of the following illustrative drawings, wherein.

DETAILED DESCRIPTION OF PREFERRED EMBODIMENTS

Figure 1:
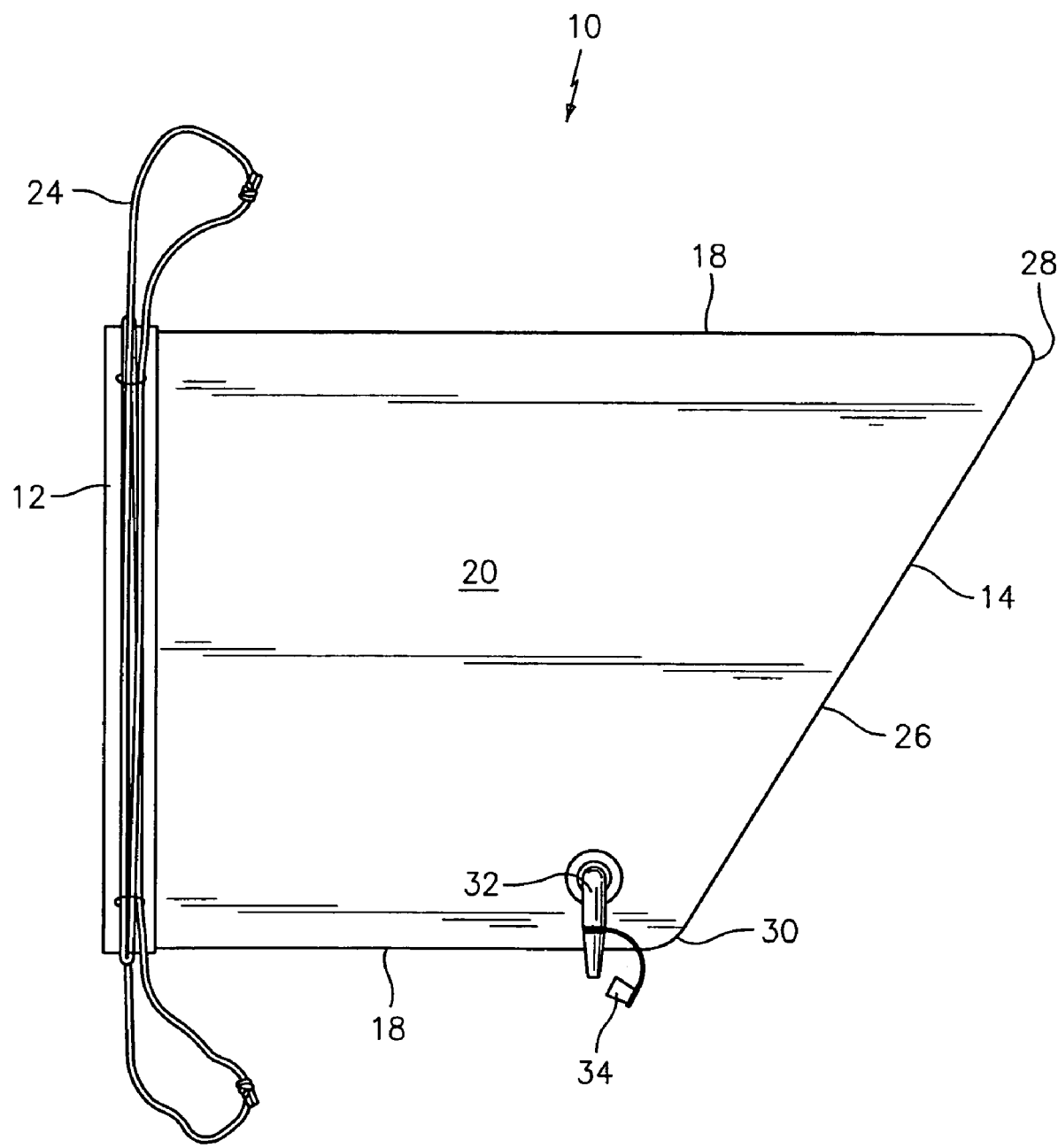
FIG. 1 is a side view of one embodiment of the medical drape of the present invention.
Figure 2:
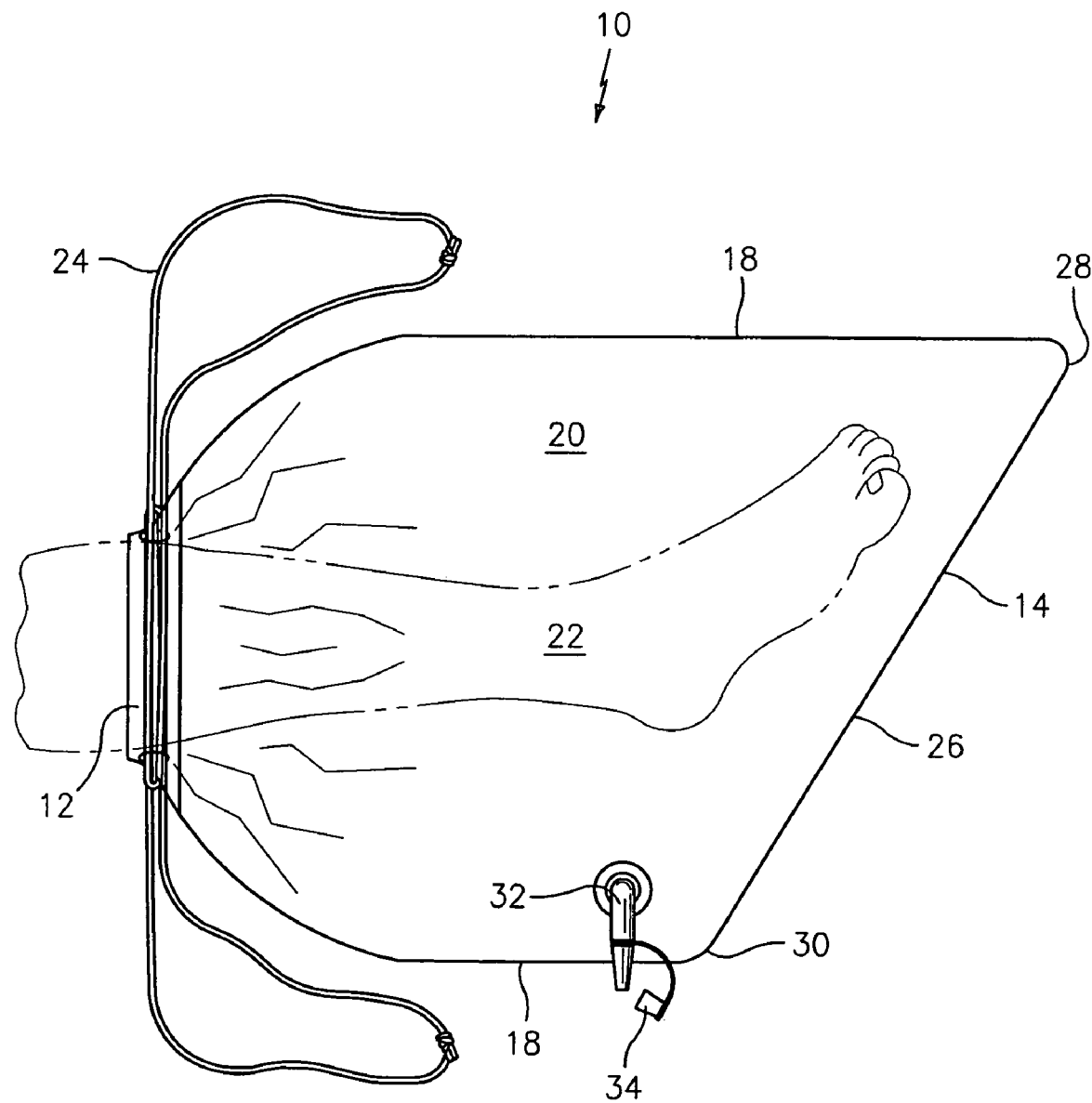
FIG. 2 is a side view of the medical drape of FIG. 1 applied to a patient's lower extremity.
Figure 3:
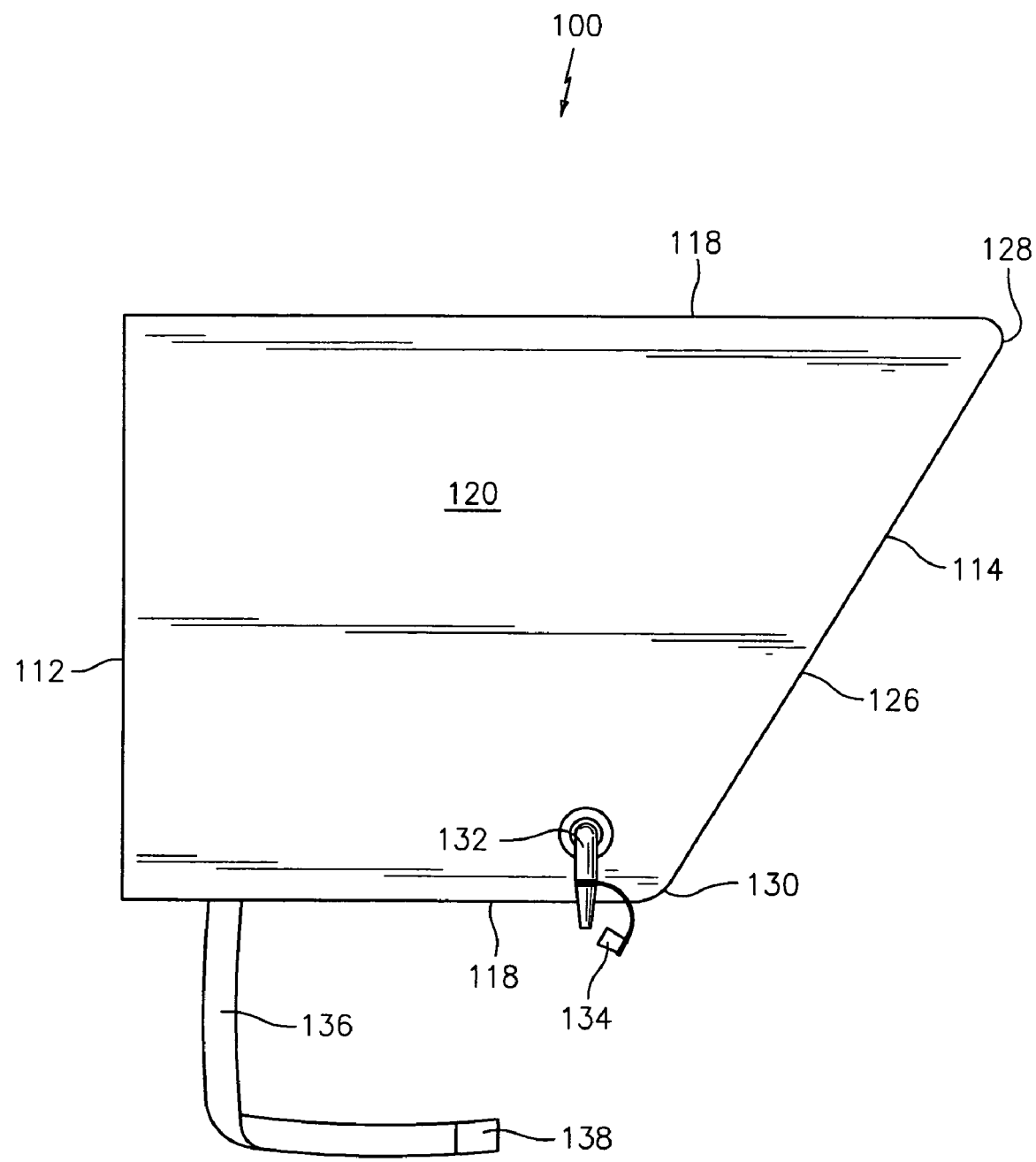
FIG. 3 is a side view of an alternate embodiment of the medical drape of the present invention.

Referring to the drawings, FIGS. 1-2 show one embodiment of the medical drape of the present invention, and FIG. 3 shows an alternate embodiment.

The medical drape of the present invention, preferably used as a surgical drape, is shown generally at 10 in FIGS. 1-2. In the preferred embodiment the drape is a transparent or translucent plastic material, as for example, polyethylene or a polyurethane, although other materials can readily be used, such as vinyl or rubber materials. The materials used should be fluid resistant and desirably should be suitable for cutting a slit therein to provide access for the surgeon in a surgical environment while leaving the drape disposed around the patient's extremity. Alternatively, a pre-cut slit may be provided in the side wall, desirably with means to open and close same, to provide convenient access.

The medical drape 10 is an elongated tube which has a front side or upper wall 12, a rear side 14, and a side wall 18 extending from the upper wall 12 to the rear side 14, with the front 12 and rear 14 sides being connected together by the side wall 18 to form an enclosure 20 which encloses the patient's extremity, as the patient's leg and foot 22 shown in FIG. 2. In the preferred embodiment the medical drape of the present invention is used on the patient's leg and foot and can be sized appropriately, i.e., the drape can have the size as shown for use on the lower portion of the leg and foot, or can have a larger size for use on the knee or upper leg. As indicated above, the drape should be fluid resistant so that fluids from the wound or from a surgical operation may be retained therein until safely disposed of from means provided for on the drape, which will be discussed below.

The front side or upper wall 12 is provided with means 24 to open and close the front side. In the embodiment of FIGS. 1-2 means 24 is a pull or tie closure means, with FIG. 1 showing the front side 12 open for easy access to the patient's extremity and FIG. 2 showing the front side 12 closed around the patient's leg 22 for safe and convenient retention of the patient's extremity therein. The rear side 14 includes a closed base wall 26 which may be closed by any desired means, as by an elongated base wall closure or an integral, closed base. The base wall 26 may also include means to open same, if desired.

The base wall 26 has a tapered configuration for fluid flow and has a first upper base wall portion 28 and a second lower base wall portion 30, with the upper and lower base wall portions being spaced from each other. Preferably, the tapered configuration of base wall 26 is an inward taper which extends inwardly towards front side 12, but if desired one can provide an outward taper which extends outwardly away from front side 12. Thus, as shown in the drawings in accordance with the preferred embodiment, the second lower base wall portion 30 is spaced closer to the front side 12 than the first upper base wall portion 28. Also, the upper base wall portion 28 has a generally triangular configuration for convenient placement of the patient's extremity. Thus, it can be seen that this preferred embodiment provides an inwardly tapered base wall for fluid drainage and collection at the lower portion of the drape adjacent the second lower base wall portion 30. The side wall 18 connects the base wall 26 with the front wall 12 and the base wall 26 extends generally at an angle with respect to the side wall, with the second lower base wall portion 30 preferably being closer to the front wall 12 than the first upper base wall portion 28. This facilitates fluid flow in the drape. Preferably, the base wall 26 extends continuously at an angle with respect to the side wall 18 and with respect to the front wall 12 to facilitate fluid flow, but naturally this can be varied if desired. For example, one may wish to provide a generally straight portion adjacent the second lower base wall portion 30. The angle of the base wall 26 with respect to the side wall 18 or upper wall 12 is generally from 30 to 90 degrees and preferably from 50 to 60 degrees.

In accordance with the present invention a drainage means 32 is provided adjacent the second lower base wall portion 30, generally positioned on side wall 18, for drainage of fluids that collect inside the drape 10. Closure means, as cap 34, may be provided to open and close drainage means 32. Naturally, any suitable drainage means may be employed with any suitable means provided to open and close same, such as, for example, a push pull drain or a vacuum hook-up to a nozzle and hose that creates a vacuum to drain fluids. The drainage means 32 or valve is adjacent the second lower base wall portion 30 and is preferably spaced therefrom, as from one-half to two inches from the second lower base wall portion 30. Alternatively, as desired, the drain can be positioned closer to the second lower base wall portion 30.

The alternate embodiment of FIG. 3 shows medical or surgical drape 100, with front side or upper wall 112, rear side 114 with closed base wall 126, and side wall 118, as in FIGS. 1-2. However, the closure for the upper wall 112 is a tie closure 136 with releasable adhesive 138 on the end thereof to open and close enclosure 120 around the patient's extremity. This provides for a simple and convenient mechanism to open and close the drape 100 around the patient's extremity. Similar to FIGS. 1-2, FIG. 3 includes tapered base wall 126, first upper base wall portion 128 and second lower base wall portion 130, and drainage means 132 with closure cap 134.

The medical or surgical drape of the present invention has significant advantages. It represents a convenient device that can be provided in a discardable form at a low cost. The valve location and drainage characteristics of the base wall provide a very simple and convenient mechanism to safely collect and discard fluids.

It is to be understood that the invention is not limited to the illustrations described and shown herein, which are deemed to be merely illustrative of the best modes of carrying out the invention, and which are susceptible of modification of form, size, arrangement of parts and details of operation. The invention rather is intended to encompass all such modifications which are within its spirit and scope as defined by the claims.

What is claimed is:

1. A medical drape, which comprises:
   an elongated tube having a front side and a rear side and a side wall, said front and rear side being connected together by the side wall to form an enclosure to enclose a patient's extremity;
   wherein said front side includes an open end with means to close said open end around the patient's extremity, and said rear side being closed by a closed base wall;
   said base wall having a first upper portion and a second lower portion, said upper and lower portions being spaced from each other, and including a base wall having a tapered configuration between the first upper portion and second lower portion for fluid flow towards the second lower portion, wherein said base wall having a tapered configuration extends generally at an angle with respect to the side wall from said first upper portion to said second lower portion to facilitate drainage, wherein said base wall having a tapered configuration extends generally inwardly towards said front side, and wherein the second lower base wall portion is spaced closer to the front side than the first upper portion; and
   a drainage means adjacent said second lower portion for drainage of fluids that collect inside said draped.

2. A drape according to claim 1, wherein said drape is a surgical drape for use during surgery on a patient's extremity and wherein the patient's extremity is positioned in the drape.

3. A drape according to claim 2, wherein said surgical drape covers a portion of a patient's limb during surgery and wherein the patient's limb is positioned in the surgical drape.

4. A drape according to claim 1, wherein said base wall having a tapered configuration extends continuously at said angle from said first upper portion to said second lower portion.

5. A drape according to claim 1, wherein said open end is closable around said extremity by a pull closure.

6. A drape according to claim 1, wherein said open end is closable around said extremity by an adhesive closure.

7. A drape according to claim 1, wherein said first upper portion has a generally triangular configuration.

8. A drape according to claim 1, wherein said angle is from 30 to 90 degrees.

9. A drape according to claim 1, wherein said elongated tube is a plastic material.

10. A drape according to claim 9, wherein said plastic material is transparent or translucent.

11. A drape according to claim 1. wherein said drainage means is located from one-half inch to two inches from said second lower portion.

12. A drape according to claim 1, wherein said drainage means includes a closure means to open and close the drainage means.

* * * * *